US006672310B1

(12) United States Patent
Streeter et al.

(10) Patent No.: US 6,672,310 B1
(45) Date of Patent: Jan. 6, 2004

(54) SELF ACTIVATED RESTRAINING DEVICE

(76) Inventors: Ramage Streeter, 607 Dana, Waco, TX (US) 76706; John W. Boothman, 145 HCR 4118, Itasca, TX (US) 76055

( * ) Notice: Subject to any disclaimer, the term of this patent is extended or adjusted under 35 U.S.C. 154(b) by 0 days.

(21) Appl. No.: 10/119,749

(22) Filed: Apr. 11, 2002

Related U.S. Application Data

(60) Provisional application No. 60/283,166, filed on Apr. 12, 2001.

(51) Int. Cl.[7] ................................ A61B 19/00

(52) U.S. Cl. .................. 128/869; 128/878; 128/879; 70/16

(58) Field of Search ......................... 128/846, 869, 128/877, 878, 879; 602/20, 23; 70/16, 17, 18, 19

(56) References Cited

U.S. PATENT DOCUMENTS

| | | | | |
|---|---|---|---|---|
| 941,250 | A | * 11/1909 | Herwicz | 70/16 |
| 3,545,237 | A | * 12/1970 | Thompson | 70/16 |
| 4,964,419 | A | 10/1990 | Karriker | 128/879 |
| 5,038,799 | A | 8/1991 | Fowler et al. | 128/878 |
| 5,349,966 | A | 9/1994 | Garcia | 128/879 |
| 5,461,890 | A | * 10/1995 | LeFavor | 70/16 |
| 5,518,010 | A | 5/1996 | Dodge | 128/869 |
| 5,551,086 | A | 9/1996 | Albanese | 2/158 |
| 5,555,751 | A | * 9/1996 | Strickland | 70/16 |

* cited by examiner

*Primary Examiner*—Michael A. Brown
(74) *Attorney, Agent, or Firm*—Patent & Trademark Services; Thomas Zack; Joseph H. McGlynn

(57) ABSTRACT

A prisoner activated restraining device which is activated when the wrists of a prisoner are placed in channels of the device.

4 Claims, 2 Drawing Sheets

SELF ACTIVATED RESTRAINING DEVICE

This invention claims the benefit of the U.S. Provisional application No. 60/283,166 filed on Apr. 12, 2001.

BACKGROUND OF THE INVENTION

The present invention relates to a restraining device for an individual which is activated by a user without any assistance from another.

DESCRIPTION OF THE PRIOR ART

Devices that are used to restrain individuals have been used throughout history. Such restraints are disclosed in a variety of configurations and sizes in the prior art. For example, U.S. Pat. No. 4,964,419 to Karriker discloses a pair of handcuffs formed of light weight plastic material formed by two loops.

U.S. Pat. No. 5,038,799 to Fowler et al. discloses a restraint system with a bar and spring loaded end pins attached to the bar and to side rails of a bed or crib and slidably mounted rings on the bar.

U.S. Pat. No. 5,349,966 to Garcia discloses a restraining device for the hands of an individual which has an inner pouch and an outer pouch over the inner pouch with securing means on the outer pouch to secure them to handcuffed wrists.

U.S. Pat. No. 5,518,010 to Dodge discloses a restraining device with a bar that has curved end segments to confine the raised upper arms of an individual. Straps on the bar are attachable to the end segments and used to restrain the arms of a user.

U.S. Pat. No. 5,551,086 to Albanese discloses a restraining device used to restrain hands and prevent the user from using their fingers and thumbs when a pair of mitts are connected to handcuffs.

In the present invention a user activated restraining device is activated when the wrists of a prisoner are placed in channels of the device permitting the officer to keep his or her hands free, all as will be detailed in the specification that follows hereafter.

SUMMARY OF THE INVENTION

This invention relates to a user activated restraining device which is activated when the wrists of a user are placed in channels of the device.

It is an object of the present invention to provide for an improved self activated restraining device.

Another object is to provide for such a device wherein the wrists of a prisoner are placed in channels which action releases an arm that restrains the user.

It is an object of the present invention to provide for an improved self activated restraining device which is easier and safer for an officer to use.

These and other objects and advantages of the present invention will become apparent to readers from a consideration of the ensuing description and the accompanying drawings.

DESCRIPTION OF THE PREFERRED EMBODIMENT

Figure 1:
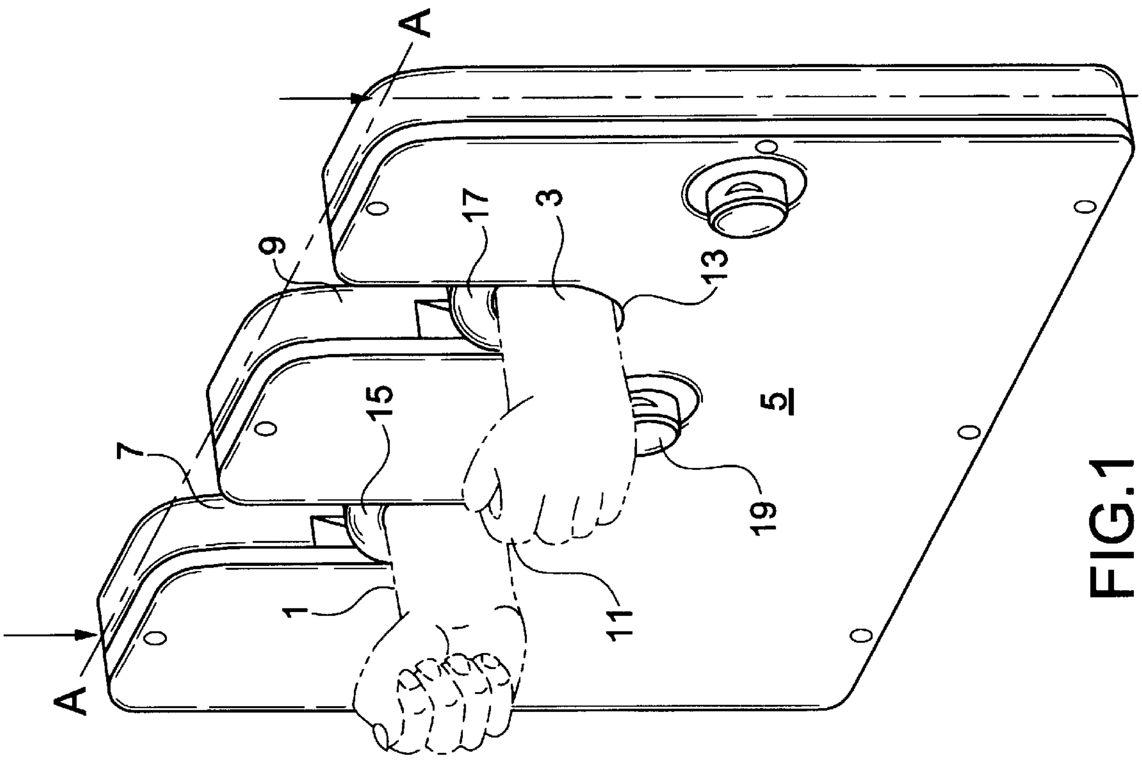
FIG. 1 is a perspective view of the present invention showing both wrists in a restrained position.

FIG. 1 is a perspective view of the present invention showing the two arms 1 and 3 of a user in a restrained position at the wrists. A housing 5 has two opened channels 7 and 9, configured to receive the lower arm portions of a user. Each channel is identical and each has a lower U-shaped portion 11 (partially obstructed from view) and 13, into which the wrist of a prisoner can rest. When in a restrained position, each wrist is held in place at the U-shaped portion by an arm 15 or 17 which fits over the lower arm near, or at the prisoner's wrist in the channel and prevents the prisoner from raising their arm. Each arm 15, 17 is configured at its engaged portion to resemble the natural curvature of a person's lower arm near or at the wrist, and is generally shaped at slightly less than a semi-circle at the engaged portion.

After the prisoner has his or her wrists secured, as shown, the law enforcement officer can applied handcuffs to the user before releasing the restraining arms 15 and 17. To release a restraining arm from its engaged position a key (not shown) is first inserted into the opening 19. Then, the key is rotated counter-clockwise ninety degrees which action releases both of the arms simultaneously. Depending on the situation, and the judgment of the officer, the prisoner can be either handcuffed before being released from the arms, may be restrained with another type of restraint or may simply be released.

Figure 2:
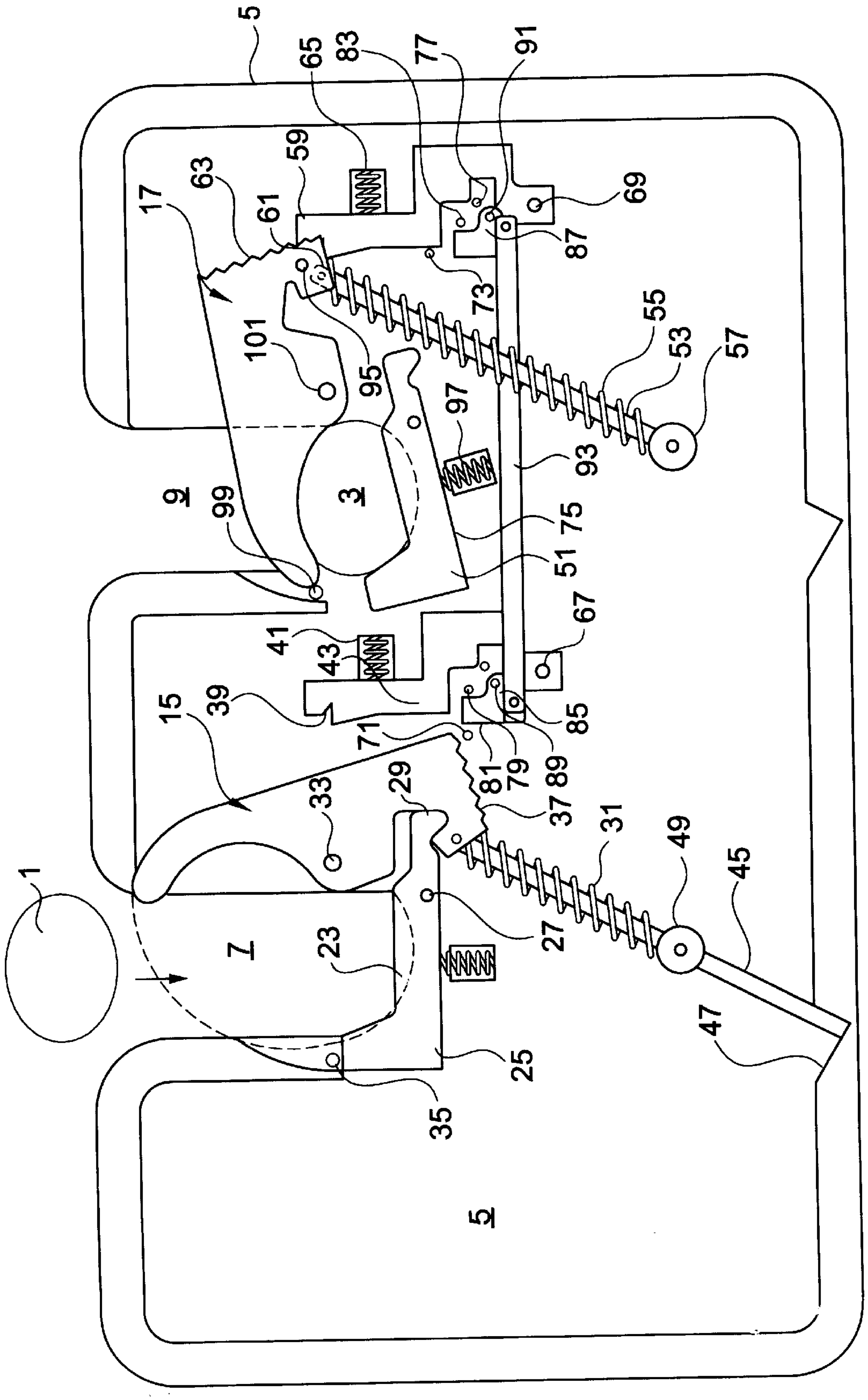
FIG. 2 is an internal view of the FIG. 1 housing when the front facing portion has been removed at the direction of the line A—A in FIG. 1.

FIG. 2 is an internal view of the housing 5 when the front facing portion has been removed at the line A—A of FIG. 1 as seen looking directly into the housing front. FIG. 2 is viewed before one of the prisoner's wrists has been placed into channel 7 and restrained by arm 15. To the right in channel 9 the other prisoner's wrist is restrained by the restraining arm 17 as in FIG. 1. As a user places his or her lower arm or wrist into the lower U-shaped portion of a channel, e.g. portion 23 of channel 7, the lower arm or wrist of a prisoner depresses a trigger (e,g. trigger 25). When trigger 25 is depressed it pivots around a supporting pivot pin 27. The engaged end of trigger 25 is released from its engagement with a depression in the retraining arm 15. A compression spring 31 drives the pivotally connected arm 15 to move in a counter-clockwise direction about the pivot pin 33. The upper end of arm 15 moves downwardly in an arc until it reaches the detent pin 35. The other end of arm 15 has a ratchet surface 37 which, when rotated, engages a ratchet surface 39 on the spring 41 biased lever 43. When the ratchet surfaces 37 of arm 15 engages the ratchet surface 39 of lever 43, a rod 45, which has spring 31 coiled around its surface, is lifted from engagement within an internal lower notch 47 of the housing frame. A pivot 49 fixed to the housing permits the rod 45 to both pivot and slide through this mounting as the rod is raised toward the pivotally mounted arm 15.

The other channel 9 has essentially the same mechanical components as in channel 7 including: the operating arm 17 with its own trigger 51, rod 53, spring 55, pivot slide 57, lever 59 with a ratchet rear surface 61 that engages back ratchet surface 63 of arm 17, and locking engagement spring 65 for lever 59. Since the levers 43 and 59 are fixed to the back wall of the housing 5 at pivot pins 67 and 69, respectively, these two spring engaged levers cannot be moved back by the prisoner applying an upward pressure on the engaged arms 15 or 17.

The prisoner's wrist, shown engaged by arm 17 in FIG. 2, is restrained or locked in place until a key is inserted to move the restraining arm. Before doing so, the officer may wish to handcuff the wrist of the prisoner. Two pins 71 and 73, fixed to the two opposite facing walls of the housing 5, prevent excess movement of the arms 15 and 17, respectively. Other wall mounted pins 75 and 77 prevent rotation of the key in the wrong direction.

To release a restrained wrist from holding arm 15 or 17 a key is inserted, key tang up, into one of the front housing openings 19 or 21, respectively, and rotated clockwise. When this happens a key pivot pin 79 associated with arm 15 is moved ninety degrees until it reaches stop pin 75. A similar release mechanism is used for the other channel arm 17.

After the prisoner removes his or her wrist from the arm 15 or 17 in the respective channel, the office may reset the arms by rotating the key counter-clockwise ninety degrees until it reaches stop pin 81 or 83 and then removes the key. The rotation of the key forces a small lever 85 (or 87) to rotate on its respective pivot joint 89 or 91 counterclockwise. Linkage rod 93 forces ratchet levers 43 and 59 to rotate clockwise simultaneously on their pivot pin mounts, thereby disengaging arms 15 and 17. When the prisoner's wrists are raised to a released position, trigger 51 rotates on pivot pin 95 clockwise by the force of spring 97 until the trigger stops at pin 99. When the wrist of a prisoner clears the top of a channel it causes restraining arm 15 or 17 to rotate clockwise around pivot pins 33 or 101 until the arm is locked into its respective trigger. The arms 15 and 17 are now reset to restrain a prisoner.

Although the preferred embodiment of the present invention and the method of using the same has been described in the foregoing specification with considerable details, it is to be understood that modifications may be made to the invention which do not exceed the scope of the appended claims and modified forms of the present invention done by others skilled in the art to which the invention pertains will be considered infringements of this invention when those modified forms fall within the claimed scope of this invention.

What we claim as our invention is:

1. A self activated restraining device comprising:

a housing having a first channel for receiving an arm portion of a prisoner, said housing having a second channel for receiving a second arm portion of said prisoner, a first self actuated lever mounted to move to an arm restraining position in the first channel, a second self actuated lever mounted to move to an arm restraining position in the second channel, and said first self actuated lever and said second self actuated lever each having separate triggers to individually move each of the self actuated levers into a restraining position when said prisoner inserts an arm portion into the first channel and the second channel, and wherein said first self actuated lever and said second self actuated lever are each pivotally mounted to the housing, and wherein said first self actuated lever and said second self actuated lever each have ratchet surfaces, and a separate lever having a ratchet surface to engage the ratchet surfaces of the first self actuated lever and the second actuated lever, each of said separate levers being spring biased for movement towards the ratchet surfaces of the first self actuated lever and the second actuated lever.

2. The device as claimed in claim 1, also including a rod having a first end and second end for each of the separate levers, each of said rods having a sliding pivot mounted to the housing and a biasing member, said biasing member of the rod permitting the first end of each rod to engage a separate lever.

3. The device as claimed in claim 2, including a key opening in the housing for inserting a key to move the first self actuated lever and the second self actuated lever from a restraining position.

4. The device as claimed in claim 3, wherein there are housing notches to receive the second end of each rod when the rod does not engage a separate lever in a self actuated lever restraining position.

* * * * *